(12) United States Patent
McDonnell

(10) Patent No.: US 7,131,205 B2
(45) Date of Patent: Nov. 7, 2006

(54) ELECTRIC POWERED ROTARY SAW

(76) Inventor: Robert L. McDonnell, 680 Oleander Rd. #8, Palm Springs, CA (US) 92264

( * ) Notice: Subject to any disclaimer, the term of this patent is extended or adjusted under 35 U.S.C. 154(b) by 147 days.

(21) Appl. No.: 10/633,704

(22) Filed: Aug. 5, 2003

(65) Prior Publication Data

US 2005/0097760 A1   May 12, 2005

(51) Int. Cl.
*B27B 9/00* (2006.01)

(52) U.S. Cl. .............................. 30/389; 30/390; 30/276

(58) Field of Classification Search ................ 30/122, 30/388, 389, 390, 275.4, 276, 307, 376; 125/13.01 125/15, 1
See application file for complete search history.

(56) References Cited

U.S. PATENT DOCUMENTS

| | | | | |
|---|---|---|---|---|
| 530,791 A * | 12/1894 | Nweton | ...................... | 83/591 |
| 1,575,577 A | 3/1926 | Guza | | |
| 2,490,255 A * | 12/1949 | Chase | ......................... | 30/371 |
| 2,787,265 A | 4/1957 | Neidt | | |
| 2,972,363 A * | 2/1961 | Ruggero | ..................... | 30/389 |
| 3,221,783 A * | 12/1965 | Kaltenmark et al. | ......... | 30/376 |
| 3,533,456 A | 10/1970 | Hovhannesian | | |
| RE27,716 E * | 8/1973 | Santilli | ........................ | 30/389 |
| 3,797,354 A * | 3/1974 | Allison | ........................ | 83/824 |
| 3,930,310 A * | 1/1976 | Santilli | ........................ | 30/389 |
| 4,316,328 A * | 2/1982 | Duggan et al. | ............... | 30/389 |
| 4,317,282 A | 3/1982 | Pace | | |
| 4,361,956 A * | 12/1982 | Kirk | ............................ | 30/122 |
| 4,593,733 A * | 6/1986 | Hamilton | .................... | 144/34.1 |
| 4,800,650 A * | 1/1989 | Johansson | ..................... | 30/389 |
| 4,841,643 A * | 6/1989 | Colella et al. | ................ | 30/500 |
| 4,972,589 A | 11/1990 | Povleski | | |
| 5,239,758 A | 8/1993 | Lindell | | |
| 5,303,471 A * | 4/1994 | Liberatoscioli | .............. | 30/122 |
| 5,369,886 A * | 12/1994 | Gallatin | ....................... | 30/371 |
| 5,755,293 A * | 5/1998 | Bourke | ........................ | 173/29 |
| 6,050,253 A * | 4/2000 | Nilsson et al. | ........... | 125/13.01 |
| 6,264,211 B1 | 7/2001 | Granado | | |
| 6,785,971 B1 * | 9/2004 | McDonnell | .................. | 30/389 |

* cited by examiner

*Primary Examiner*—Boyer D. Ashley
*Assistant Examiner*—Omar Flores Sánchez
(74) *Attorney, Agent, or Firm*—Dennison, Schultz & MacDonald

(57) ABSTRACT

An electric powered rotary saw for cutting medical cast or the like includes a cylindrical housing, a removable longitudinally extending mounting member and a rotary circular saw blade disposed at one end of the mounting member. The saw blade is fixed to a shaft for rotation about an axis which is generally perpendicular to the longitudinal axis of the mounting member, but slightly offset therefrom. A variable speed electric motor is disposed in the housing and includes a shaft which extends forwardly in a direction parallel with a mounting portion of the longitudinal member. A frusto-conical driver member of an elastomeric material is fixed to the end of the shaft and engages the circular blade to displace a portion of the blade out of its normal plane of rotation by an angle of about 5 degrees and for rotating a circular blade.

4 Claims, 4 Drawing Sheets

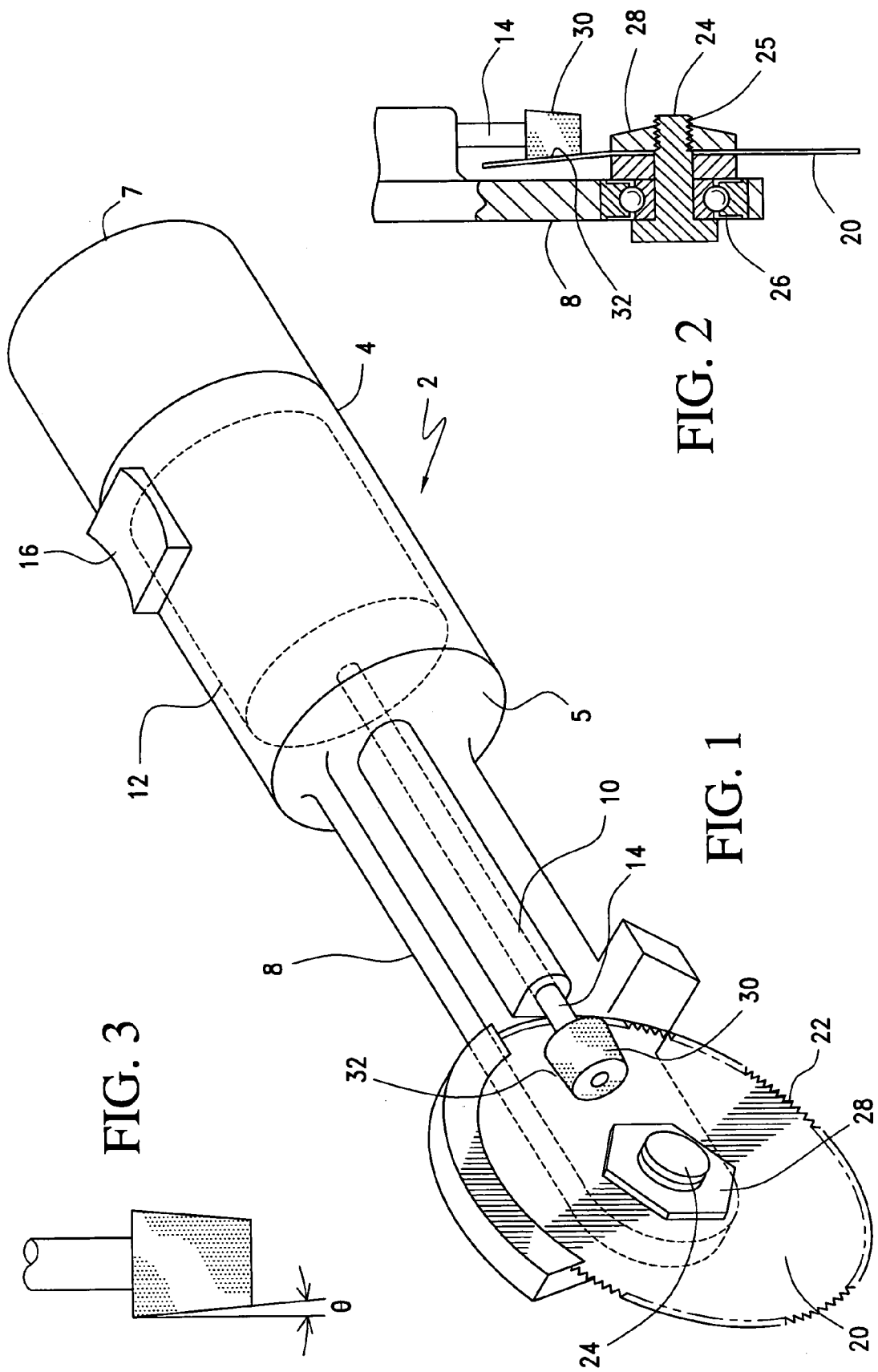

US 7,131,205 B2

ELECTRIC POWERED ROTARY SAW

FIELD OF THE INVENTION

This invention relates to an electric powered rotary saw for cutting medical casts or the like and more particularly to an electric powered rotary saw with a removable mounting member for positioning a saw blade to rotate in a plane Which is generally parallel with a rotatable shaft but angularly offset therefrom of an angle of about 0° to 30°.

BACKGROUND OF THE INVENTION

Annular saws that rotate and which are driven by the friction of a roller acting on a saw blade are well known. For example, the Santilli U.S. Pat. No. Re 27,716 discloses an annular saw with a circular safety guard. As disclosed therein conical rollers rotate an annular saw blade about an axis. This saw blade includes a plurality of cutting teeth about the periphery of the blade. A portion of the saw blade is protected by a casing. As disclosed, in the patent, the saw blade is provided with a circular guard which conceals nearly the entire saw blade's tooth periphery and gradually exposes it only when the workpiece is fed to the saw.

Apparatus for damping vibrations of rotary cutting blades are also known. For example, the U.S. Patent of Allison, U.S. Pat. No. 3,797,354 discloses such apparatus. As disclosed therein, the planar surface of a rotary cutting blade is frictionally contacted by a damping means comprising a plurality of coaxial independent rotatable discs each presenting a relatively narrow peripheral surface in contact with the planar surface and intersecting the axis of rotation of the cutting blade. The apparatus includes a frusto-conical surface or a plurality of spaced coaxially frusto-conical roller segments. Means are provided for adjusting the frictional contact between the damping means and the planar surface.

My copending application entitled Electric Powered Rotary Hacksaw, Ser. No. 10/314,979 which was filed on Dec. 10, 2002 discloses an electric powered rotary hacksaw which includes a cylindrical housing, an integral longitudinally extending mounting member and a rotary circular hacksaw blade disposed on one end of the mounting member. The hacksaw blade is fixed to a shaft for rotation about an axis which is generally perpendicular to the longitudinal axis of a mounting member. A variable speed electric motor is disposed in the housing and includes a shaft, one end of which extends outwardly out of the housing in a direction which is generally parallel with a longitudinal member. A frusto-conical driver made of an elastomeric material is fixed to the end of the shaft and engages the circular blade to displace a portion of the blade out of the normal plane of rotation by an angle of about 5° and for rotating the circular blade.

Notwithstanding the above, it is presently believed that there may be a commercial demand for an improved electric powered rotary saw in accordance with the present invention. It is believed that there may be a demand for an improved electric powered rotary saw for cutting medical casts and for other applications. It is also believed that there may even be a greater commercial demand for an adapter in accordance with the present invention which enables an individual to convert a conventional electric powered rotary saw to an electric powered rotary saw in accordance with the present invention.

Further, the improved electric powered electric saw and adapter in accordance with the present invention are relatively light in weight, free from unnecessary vibration, durable, can be manufactured and sold at competitive prices and adaptable to various applications.

SUMMARY OF THE INVENTION

In essence, the present invention contemplates an electric powered rotary saw comprising a housing and a removable longitudinally extending mounting member extending forwardly from the housing. The rotary saw includes a circular blade having a generally planar surface and a cutting surface or plurality of cutting teeth along a peripheral edge thereof. The cutting blade also includes a driving portion inwardly from the cutting surface and preferably nearer to the cutting teeth then to the center of rotation. The cutting blade is disposed in a first plane and is rotatable about a first axis of rotation. An electric motor is disposed in the housing and includes a rotatable shaft which is rotatable about a second axis of rotation which is generally transverse of the first axis of rotation. An elastomeric preferably a relatively hard rubber frusto-conical driver is disposed on a rotatable shaft for rotation by the electric motor. The elastomeric driver is brought into contact with the driving portion of the cutting blade to rotate the blade about the first axis and to displace the driving portion and cutting teeth of a blade out of the first plane.

The invention will now be described in connection with the accompanying drawings wherein like reference numerals have been used to define like parts.

BRIEF DESCRIPTION OF THE DRAWINGS

FIG. 1 is a perspective view of an electric powered rotary hacksaw in accordance with a first embodiment of my earlier invention as disclosed in my copending application Ser. No. 10/314,979;

FIG. 2 is a cross-sectional view of rotary hacksaw in FIG. 1;

FIG. 3 is a schematic view showing the angle of deviation of the cutting wheel caused by the frusto-conical driving member as disclosed in my earlier application;

DETAILED DESCRIPTION OF THE PREFERRED EMBODIMENTS OF THE INVENTION

Figure 5:
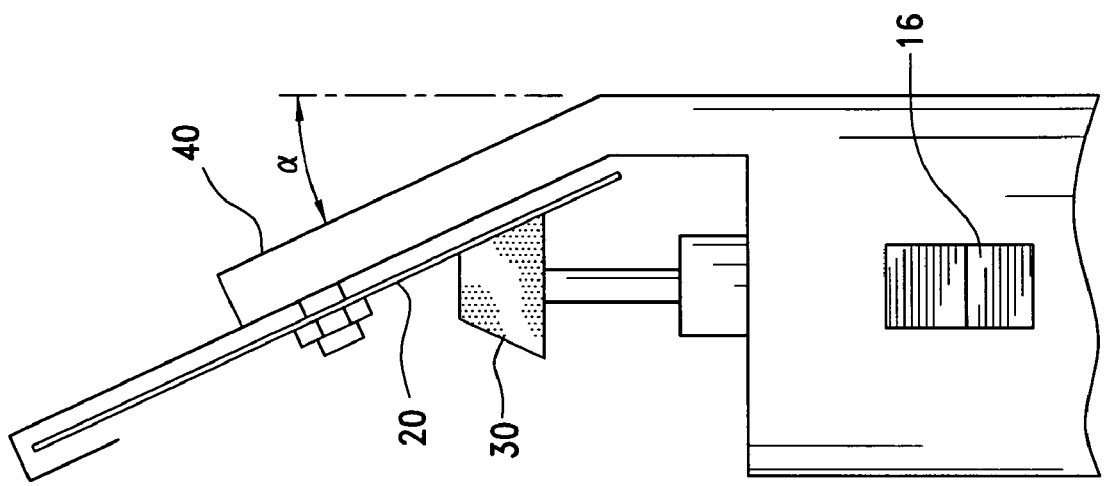
FIG. 5 is a top or plane view of the electric powered rotary hacksaw in accordance with a second embodiment of my earlier invention as disclosed in the aforementioned application.

FIGS. 1–5 illustrate my earlier invention which provide the foundation for my present invention. The present invention is an improvement of the earlier invention which is directed primarily to an electric powered rotary hacksaw for use in cutting copper tubes. By contrast, the present invention is believed to be more applicable to the medical field and for cutting casts. The present invention is also applicable for use with a conventional power unit and/or for modifying a conventional cast saw to provide inline cutting.

My earlier invention will now be described in connection with FIGS. 1–3. As illustrated therein, an electric powered rotary hacksaw 2 includes a housing 4 which is preferably made of a hard light weight plastic body having a generally cylindrical shape with two closed ends 5 and 7. The housing 4 may be formed of any strong light weight metal or plastic and preferably a low cost plastic. In a preferred form, the housing 4 is formed by injection molding or other thermal forming process and may be formed as a monolithic unit with a separate and removable end portion 7.

A longitudinally extending mounting member 8 extends outwardly or forwardly from the closed end portion 5 of the housing 4 and is preferably integral with the housing 4. In a preferred form of the earlier invention, the mounting member 8 extends forwardly of the housing 4 along an axis that is parallel or coaxial with the axis of the cylindrical housing and includes an outwardly projecting portion or shaft support 10 which defines a hollow passage way passing therethrough.

A variable speed electric motor 12 is disposed in the housing 4 in a conventional manner and includes a shaft 14 which extends through the passage in the shaft support 10. The high-speed electric motor may be battery powered or connected to a source of electricity to provide DC current to energize the motor in a conventional manner. A conventional switch 16 is used to actuate and control the speed of the variable speed motor.

An annular and preferably a circular hacksaw blade 20 includes a plurality of cutting teeth 22 disposed along a peripheral edge thereof. The cutting teeth may be in the form of diamonds as will be well understood by persons of ordinary skill in the art. The blade 20 is fixed at a forward end of a mounting member 8 by means of a rotatable shaft 24. As shown in more detail in FIG. 2, the shaft 24 is mounted for rotation about an axis which is perpendicular to an axis of shaft 14 and the mounting member 8. The shaft 24 is supported at the forward end of the mounting member 8 by a bearing assembly 26 in a conventional manner. As will be explained in greater detail herein, the blade 20 has a slight offset orientation relative to the shaft 24.

The shaft 24 also includes a threaded end portion 25 and a pair of clamping members 28 for clamping the cutting wheel 20 on the shaft 24. In a preferred embodiment of my earlier invention, a forwardly extending safety guard 35 is attached to the mounting member 8.

A frusto-conical element or driver 30 is fixed to the end of the shaft 14 in a conventional manner for rotation by the motor 12. The frusto-conical element or driver 30 includes a peripheral surface which defines an angle of about $\ominus$ of about 1° to 5° or up to 7° or 8° degrees and preferably about 3° degrees with respect to its axis of rotation as shown more clearly in FIG. 3. The length of the driver 30 and angle of inclination are such that the frusto-conical driver 30 engages a driving portion 32 of the blade 20 and exerts a slight lateral force to displace the blade 20 by about 3° degrees as shown in FIG. 2 and rotates the blade without slippage across its line of contact. This offset orientation of the blade 20 about its rotational axis alleviates vibrations of the blade commonly associated with conventional rotary hacksaws and provides for a more accurate and clean cut line. Nevertheless, the driver 30 may slip if excessive pressure is applied to the blade in cutting a piece of tubing.

Figure 4:
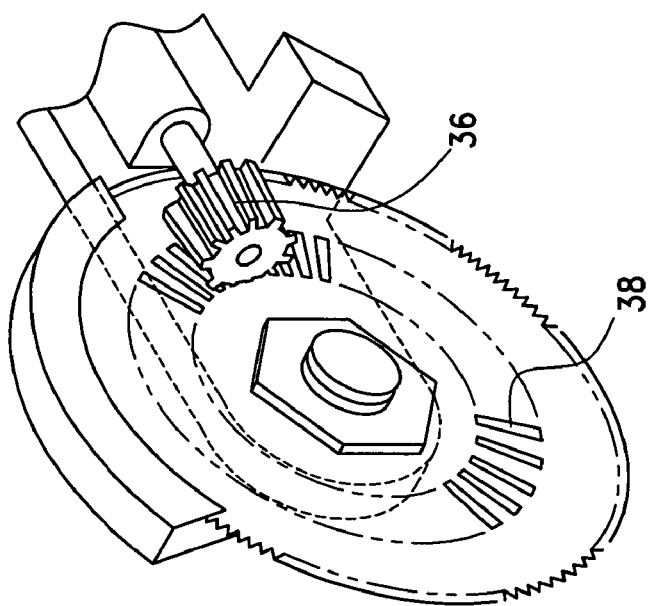
FIG. 4 is a perspective view of the alternative embodiment of the blade and the driver element as disclosed in my earlier application.

The frusto-conical element is made of an elastomer and preferably of a hard rubber or the like with a textured surface. It may have a metal core, however the outer textured surface should be of an elastomer to provide a friction drive to rotate the blade 20. In a preferred embodiment, the driver 30 is made of a synthetic rubber having a desired hardness based on International Rubber Hardness Degrees Standard as will be well understood by persons of ordinary skill in the art. The cutting blade 20 may be made of carbon steel, Carborundum, silicon carbide, or the like as used in a conventional hacksaw blade. Such blades may for example be made of HSS or HSS-SL steel or other material as will be well understood by persons or ordinary skill in the art of designing and manufacturing hacksaw blades. Alternatively, as best seen in FIG. 4, the driver may include a fluted 36 outer surface which engages a plurality of corresponding slots 38 on the blade.

Referring now to FIG. 5, an alternative embodiment of my earlier invention is illustrated. In this embodiment, the longitudinally extending mounting member includes an angled portion 40, which is slightly angled to the left at an angle $\propto$. This allows for the cutting debris to be directed away from the user and the angled mounting member provides for better viewing of the object being cut. This saw may also be useful in the medical profession. As a non-limiting example, $\propto$ may be about 30°. Moreover, this embodiment allows a right-handed user to use the rotary saw as oriented in FIG. 5, or the rotary saw may be rotated 180° along its longitudinal axis so that it can be held by a left-handed user.

Figure 6:
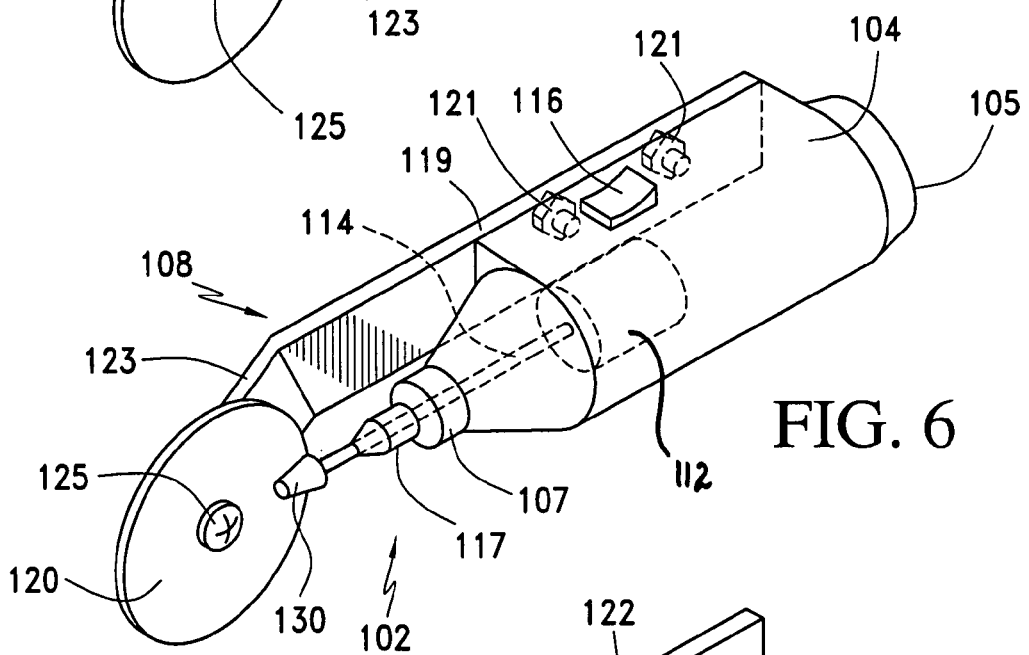
FIG. 6 is a perspective view of a rotary saw in accordance with one embodiment of my present invention.

The present invention will now be described in connection with FIGS. 6–9. As illustrated in FIG. 6, an electric powered rotary saw 102 which is particularly applicable for cutting medical casts includes a longitudinally extending housing 104. The housing 104 is preferably made of a light weight plastic material, but may be made of metal or other suitable material as will be well understood of persons of ordinary skill in the art.

The housing 104 has a generally cylindrical shape with two ends 105 and 107. A first of the ends 105 is fully closed and preferably an integral part of the housing 104. It should be recognized that the housing 104 may be formed in two halves wherein a portion of the closed end 105 is formed in each half. However, the second or forward end 107 may be removable and includes a small opening for a rotatable shaft 114 to extend therethrough.

An electric motor 112 is disposed within the housing 104 in a conventional manner. The motor 112 drives the shaft 114 in response to a source of energy (not shown) when the switch 116 is turned to an on position. The source of power may be a battery pack or other source of electrical energy such as a transformer connected to a wall socket or the like.

It is also contemplated that an electric powered rotary saw in accordance with the present invention may utilize the housing motor and rotary shaft of a conventional rotary cast saw in which the blade rotates in a plane which is perpendicular to the longitudinally extending shaft. It is also contemplated that the present invention can be used to convert a conventional cast saw to provide a fore and aft cut and when desired to convert the saw to a rotary saw with a perpendicular cut.

Figure 8:
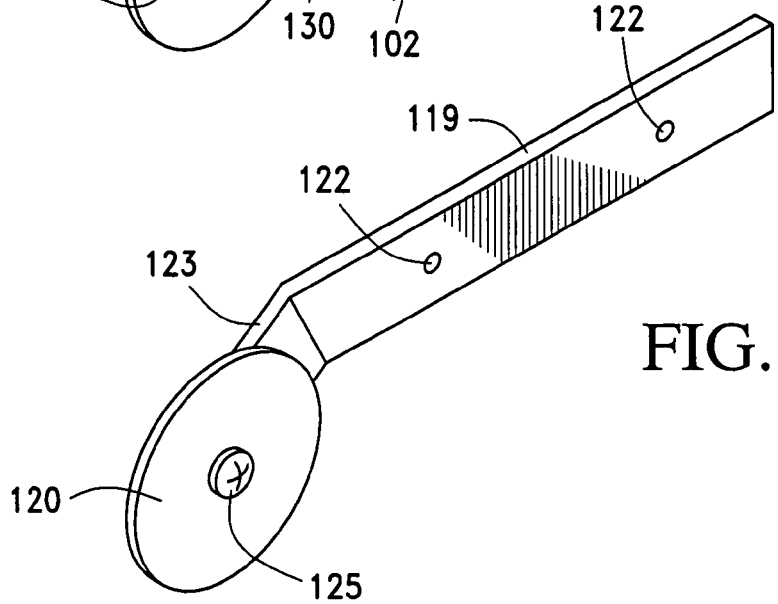
FIG. 8 is a perspective view of an attachment for a rotary saw as illustrated in FIG. 6.

The electric powered rotary saw 102 also includes a longitudinally extending removable mounting member 108 which extends forwardly from the end 107 and a chuck 117. As shown in FIGS. 6 and 8, the mounting member 108 includes a generally flat longitudinally extending portion 119 which may include a slight curvature which is compatible with the shape of the housing 104 and is removably fixed to the housing 104 by means of a pair of relatively shallow screws 121. The screws 121 may be self tapping or include a fine thread which is adapted to screw into a threaded tap hole (not shown) in the housing 104.

The mounting member 108 also includes a forward portion 123 which is offset by an angle of about 5° from the flat portion 119. The forward portion 123 of the mounting member 108 also includes a rotatable hub assembly 125 which may be of the same type as shown in FIG. 2. For example, the shaft 24 may be mounted for rotation about an axis which is substantially perpendicular to an axis of the shaft 114 (FIG. 5). The shaft 24 (FIG. 2) is supported by a bearing assembly 26 in a conventional manner.

Because of the offset angle of the forward portion of the mounting member 108, the angle of the saw blade 120 with respect to the shaft 114 corresponds to or is approximately the same as the angle of the peripheral surface of the frusto-conical driver 130.

As in my earlier invention, the length of the driver 130 and angle of inclination are such that the fusto-conical driver 130 engages a driving portion of the blade 120 and exerts a slight lateral force to displace the blade 120 slightly to minimize slippage. It is also believed that this slight pressure will reduce vibration.

Figure 7:
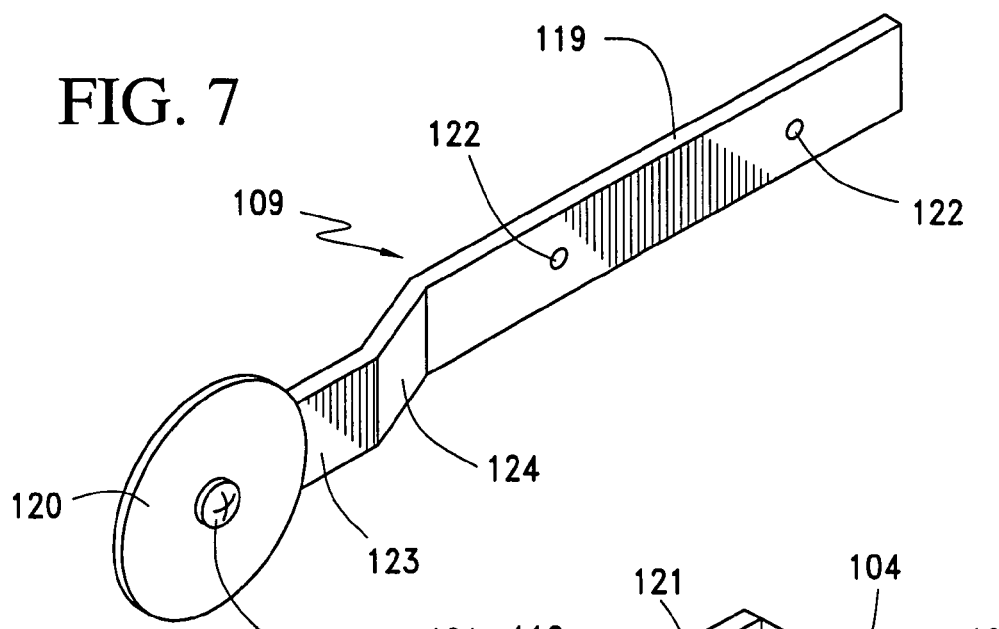
FIG. 7 is a perspective view of an attachment for a rotary saw in accordance with another embodiment of the invention.

A modified forward mounting member 109 is illustrated in FIG. 7. As illustrated therein, the forward mounting member 109 includes a generally flat longitudinally extending portion 119 having a plurality of screw receiving apertures 122 thereon, and a forward portion 125 which is offset from the flat portion 119 by an intermediate portion 124. In this embodiment of the invention, the saw blade 120 provides a cut which is generally parallel if not parallel to the axis of the shaft 114.

Figure 9:
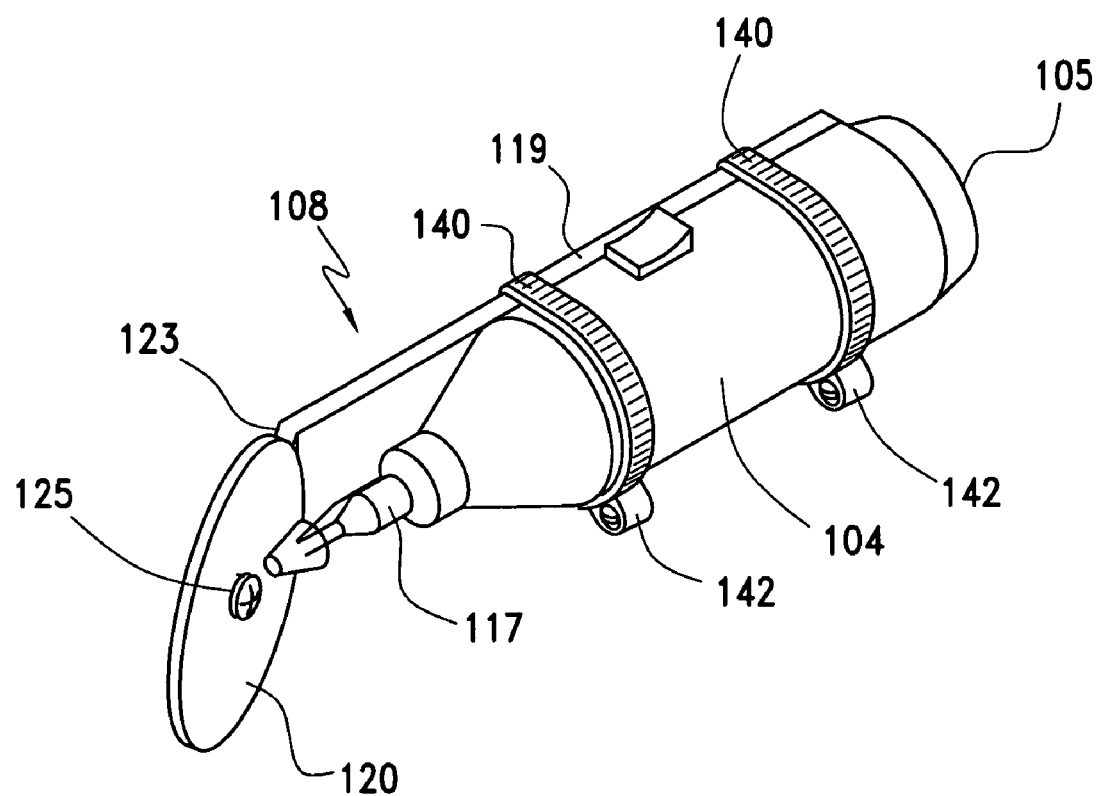
FIG. 9 is a perspective view of a rotary saw in accordance with a further embodiment of the invention.

FIG. 9 illustrates a further embodiment of the invention wherein a pair of metal or plastic bands 140 and tightening screws 142 are used to hold the forward mounting member 108 to the housing 104. Such mounting means may be advantageous in converting a conventional cast saw with a perpendicular blade to a cast saw with a fore-aft cut i.e. a cut which is parallel or nearly parallel to the longitudinal axis of the housing 104 and/or shaft 114.

In the various embodiments of the invention, the saw blade 120 is of conventional design and may be of metal or ceramic. In the later case, the flat surface of the blade may be used as an abrasive media for grinding such as removal of callouses or the like.

While the invention has been described in connection with its preferred embodiment, it should be recognized and understood that changes and modifications can be made therein without departing from the scope of the appended claims.

What is claimed is:

1. An electric powered rotary saw comprising a housing, a longitudinally extending mounting member and means for removably fixing said mounting member to said housing with a forwardly extending portion extending forwardly from said housing, an annular rotary saw blade having a generally planar surface and a cutting portion along a peripheral edge thereof, said saw blade having a driven portion inwardly of said cutting portion and rotatable in a first plane about a first axis of revolution which is generally perpendicular to said first plane, an electric motor disposed in said housing and including a rotatable shaft rotatable about a second axis of rotation which is generally transverse of said first axis of revolution, an elastomer frusto-conical driver disposed on said rotatable shaft and in contact with said driven portion of said saw blade for rotating said saw blade in response to the rotation of said shaft, and wherein said mounting member includes an angular deviation from its longitudinal axis that is about equal to the angular taper of said frusto-conical driver.

2. An electric powered rotary saw according to claim 1, in which said longitudinally extending mounting member is generally parallel with said housing over a substantial portion thereof.

3. An electric powered rotary saw according to claim 1, in which said means for removably fixing said mounting member to said housing includes a plurality of threaded openings in said housing and a plurality of screws with matching threads to fix said mounting member to said housing.

4. An electric powered rotary saw according to claim 1, in which said means for fixing said mounting member to said housing includes a strap extending around said housing and fixed to said mounting member. substantial portion thereof.

* * * * *